US012758683B2

(12) United States Patent
Dong et al.

(10) Patent No.: US 12,758,683 B2
(45) Date of Patent: Oct. 13, 2026

(54) DECELLULARIZED HEART VALVE (DHV) COMPOSITE, AND PREPARATION METHOD AND USE THEREOF

(71) Applicant: UNION HOSPITAL TONGJI MEDICAL COLLEGE HUST, Wuhan (CN)

(72) Inventors: Nianguo Dong, Wuhan (CN); Ying Zhou, Wuhan (CN); Weihua Qiao, Wuhan (CN); Ge Yan, Wuhan (CN); Shuyu Wen, Wuhan (CN); Xing Chen, Wuhan (CN)

(73) Assignee: UNION HOSPITAL TONGJI MEDICAL COLLEGE HUST, Wuhan (CN)

( * ) Notice: Subject to any disclaimer, the term of this patent is extended or adjusted under 35 U.S.C. 154(b) by 385 days.

(21) Appl. No.: 18/364,562

(22) Filed: Aug. 3, 2023

(65) Prior Publication Data

US 2024/0131223 A1 Apr. 25, 2024
US 2024/0226379 A9 Jul. 11, 2024

(30) Foreign Application Priority Data

Oct. 25, 2022 (CN) ......................... 202211310215.4

(51) Int. Cl.
*A61L 27/36* (2006.01)

(52) U.S. Cl.
CPC ......... *A61L 27/3625* (2013.01); *A61L 27/367* (2013.01); *A61L 27/3687* (2013.01); *A61L 2430/20* (2013.01); *A61L 2430/40* (2013.01)

(58) Field of Classification Search
CPC ............... A61L 27/3625; A61L 27/367; A61L 27/3687; A61L 2430/20; A61L 2430/40; A61L 2400/02; A61L 27/54; A61L 27/02; A61L 27/3641; A61L 27/50
See application file for complete search history.

(56) References Cited

FOREIGN PATENT DOCUMENTS

| | | | | |
|---|---|---|---|---|
| CN | 114634763 A | * | 6/2022 | ............... C09D 7/61 |
| WO | WO-2016023494 A1 | * | 2/2016 | ............... C09D 7/40 |
| WO | WO-2025208090 A1 | * | 10/2025 | ............. A61L 27/54 |

OTHER PUBLICATIONS

Qiao S, et al "Crosslinking Strategies of Decellularized Extracellular Matrix in Tissue Regeneration" J. Biomed. Mater. Res., Part A,(2024), 112(5), pp. 640-671; doi:10.1002/jbm.a.37650. (Year: 2024).*
Yang Z, et al, WO-2016023494-A1, machine translation, 63 pages (Year: 2016).*
Mayer J, et al, WO-2025208090-A1, machine translation, 148 pages (Year: 2025).*
Yang, Z, CN-114634763-A, machine translation, 43 pages (Year: 2022).*
Wagers, Amy "Aging and GDF11: What we know" Harvard Stem Cell Institute (HSCI), (retrieved from URL: <www.hsci.harvard.edu/aging-and-gdf11-what-we-know>, 3 pages (Year: 2026).*

* cited by examiner

*Primary Examiner* — Aaron J Kosar
(74) *Attorney, Agent, or Firm* — JEEN IP LAW, LLC

(57) ABSTRACT

Some embodiments of the disclosure provide a decellularized heart valve (DHV) composite, a preparation method of the DHV composite, and a use of the DHV composite. In some examples, the preparation method of the DHV composite includes the following steps: S1, conducting a reaction I on a DHV with a copper chloride-dopamine hydrochloride mixed solution to obtain a copper ion-modified DHV; and S2, conducting a reaction II on the copper ion-modified DHV with a GDF11 solution to obtain the DHV composite. In other examples, the present disclosure provides a use of the DHV composite in preparation of a tissue-engineered heart valve (TEHV). In further examples, the TEHV is a heart valve (HV) with remodeling and regeneration capabilities.

7 Claims, 12 Drawing Sheets

DECELLULARIZED HEART VALVE (DHV) COMPOSITE, AND PREPARATION METHOD AND USE THEREOF

CROSS REFERENCE TO RELATED APPLICATIONS

This application claims priority to Chinese patent application number 202211310215.4, filed on Oct. 25, 2022, the disclosure of which is incorporated by reference herein in its entirety.

FIELD OF THE DISCLOSURE

The disclosure relates generally to the field of medical devices. More specifically, the disclosure relates to decellularized heart valve (DHV) composites, preparation methods thereof, and uses thereof.

BACKGROUND

Valvular heart disease refers to narrowing and/or regurgitation of heart valves caused by various etiologies. This disease has high incidence rate and mortality, and seriously threatens human health. Valve replacement surgery is the most effective treatment for valvular heart diseases, and there is a huge demand for artificial valve substitutes. Clinically, the existing valve substitutes are mainly mechanical valves and biological valves. The mechanical valve has the risk of bleeding and thrombosis, and patient needs to take anticoagulant drugs for life. The biological valve is prone to calcification and decay, and has an average service life of only 10 years to 15 years. In addition, none of these artificial valves can grow autonomously. The growth and development of children after surgery generally lead to a size of the original valve no longer matching, resulting in unavoidable secondary surgery.

The next-generation tissue-engineered heart valves (TEHVs) are a new direction in the development of valve substitutes. The TEHV theoretically has self-healing properties, adaptive remodeling growth, antithrombotic ability, and low immunogenicity. Therefore, TEHV is expected to solve the dilemma faced by clinical valve substitutes and has a desirable prospect for transformation.

Decellularized heart valve (DHV) is an extracellular matrix obtained by removing cellular components from allogeneic or heterogeneous heart valves (HVs) by chemical detergents, enzymatic hydrolysis, or physical methods. The DHVs are widely used in TEHV construction. Through a proper decellularization process, DHV has greatly reduced its immunogenicity, while well preserving native valve morphology and three-layer structure. Moreover, the DHV contains many biologically active molecules, which help to regulate the biological behavior of seed cells and provide clues for the tissue regeneration of the valve in situ.

However, after being implanted into the human body, pure DHV products (such as CryoValve from CryoLife Company) do not have effective coverage of autoendothelial cells, showing a poor clinical application effect. In the early stage of DHV implantation, due to the lack of endothelial cell coverage, the surface of DHV quickly adsorbs plasma proteins, promoting the adhesion and activation of platelets and leukocytes. As a result, the risk of thrombosis and embolism is increased, thus affecting valve functions and remodeling and regeneration processes.

Therefore, pure DHVs need to be further modified to improve blood compatibility and accelerate endothelialization to ensure the in vivo performance of the valve material and achieve the in vivo remodeling and regeneration.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, a first aspect of the present disclosure relates to a preparation method of a DHV composite, including the following steps.

S1, conducting a reaction I on a DHV with a copper chloride-dopamine hydrochloride mixed solution to obtain a copper ion-modified DHV.

S2, conducting a reaction II on the copper ion-modified DHV with a GDF11 solution to obtain the DHV composite.

Optionally, step S1 includes the following steps.

S11, mixing the DHV with the copper chloride-dopamine hydrochloride mixed solution, and conducting the reaction I.

S12, removing the copper chloride-dopamine hydrochloride mixed solution, and rinsing an obtained reacted DHV with a rinsing solution.

S13, obtaining the copper ion-modified DHV.

Optionally, the copper chloride-dopamine hydrochloride mixed solution has a pH value of 8 to 9, optionally 8.5; and the copper chloride-dopamine hydrochloride mixed solution has 0.005 mg/ml to 0.2 mg/ml, optionally 0.1 mg/ml of $CuCl_2 \cdot 2H_2O$ and 0.1 mg/ml to 5 mg/ml, optionally 0.2 mg/ml of dopamine hydrochloride.

Optionally, in step S1, the copper chloride-dopamine hydrochloride mixed solution is prepared with a tris(hydroxymethyl)aminomethane hydrochloride (Tris-HCl) solution at a concentration of 1.2 mg/ml.

Optionally, after the DHV is mixed with the copper chloride-dopamine hydrochloride mixed solution, a resulting mixture I is subjected to the reaction I in an environment of 25° C. to 40° C.; optionally, after the DHV is mixed with the copper chloride-dopamine hydrochloride mixed solution, the mixture I is subjected to the reaction I in any constant temperature of 36° C. to 37.5° C. (conventional constant-temperature requirements), optionally 37° C.

Optionally, step S2 includes the following steps.

S21, mixing the copper ion-modified DHV obtained in step S1 with the GDF11 solution, and conducting the reaction II.

S22, removing the GDF11 solution, and rinsing an obtained reacted copper ion-modified DHV with a rinsing solution.

S23, obtaining the DHV composite.

Optionally, in step S21, the GDF11 solution is prepared by a phosphate-buffered saline (PBS) solution; and in step S21, the GDF11 solution has a concentration of 0.5 μg/ml. In step S21, after the copper ion-modified DHV is mixed with the GDF11 solution prepared by the PBS solution, a resulting mixture II is subjected to the reaction II in any constant temperature of 36° C. to 37.5° C., optionally 37° C. On the basis of step S2, a reaction process is shown in a reaction formula of FIG. 8.

Optionally, in steps S12 and S22, the rinsing solution is a PBS solution, and a rinsing process includes following steps: placing the reacted DHV or the reacted copper ion-modified DHV in a constant-temperature shaker, washing with a sterile PBS solution for 24 h, and changing the sterile PBS solution once every 6 h; in steps S11, S12, S21, and S22, the constant-temperature shaker has an oscillation frequency of 110 rpm; and in step S1, the DHV is a natural DHV, including decellularized porcine aortic valve or bovine pericardium.

The natural DHV (porcine aortic valve and bovine pericardium) may be treated using existing technologies, such as a technology discussed in patent 201610921956.4 for decellularization.

In other embodiments, a second aspect of the present disclosure provides a DHV composite prepared by the preparation method. Of course, it is not strictly limited that the DHV composite must be exactly the same as a material prepared by the aforementioned preparation method. Products obtained by changing part of the preparation conditions should also be considered equivalent as long as they have the same or similar properties as those of the present disclosure.

In further embodiments, a third aspect of the present disclosure provides use of the DHV composite in preparation of a TEHV scaffold material in regenerative medicine. Specifically, it is embodied in use of the DHV composite in preparation of a TEHV, especially use in preparation of a HV with remodeling and regeneration capabilities. This valve is especially suitable for children with valvular heart disease, and may reshape its growth with the normal growth and development of children to keep the size matching, thereby avoiding children from undergoing multiple valve replacement operations. One application of HV with the capability to remodel and regenerate is the treatment of valvular heart disease in children.

BRIEF DESCRIPTION OF THE DRAWINGS

Illustrative embodiments of the present disclosure are described in detail below with reference to the attached drawing figures.

DETAILED DESCRIPTION

Figure 1:
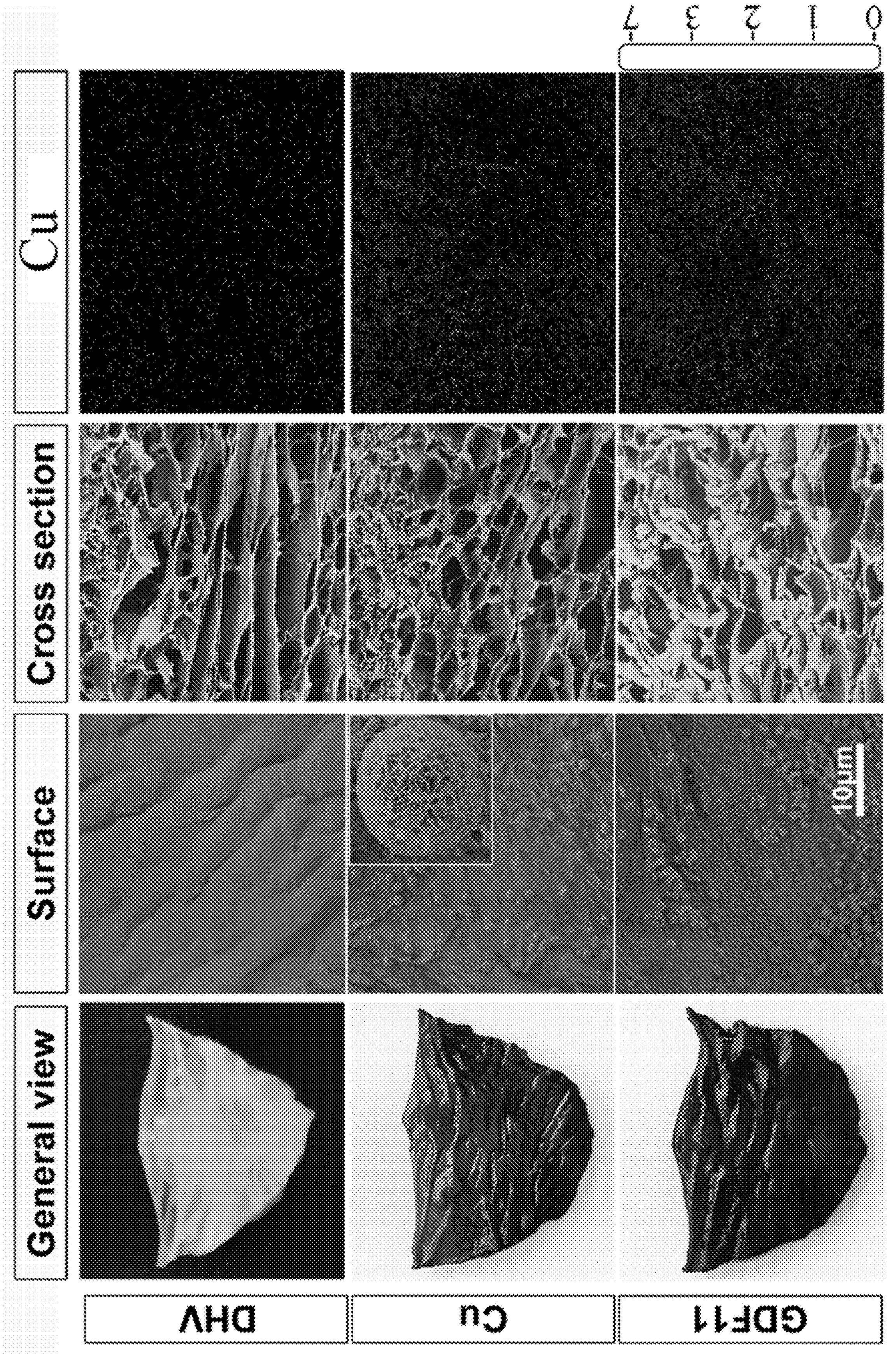
FIG. 1 shows a naked eye general view and a scanning electron microscopy (SEM) image of a DHV composite according to an embodiment of the disclosure.

The following describes some non-limiting exemplary embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

The present disclosure is further described below with reference to the accompanying drawings and specific examples, but the present disclosure is not limited thereto.

A preparation method of a DHV composite may include the following steps:

S1, preparation of a copper ion-modified DHV: a copper chloride-dopamine hydrochloride mixed solution (containing 0.1 mg/ml of copper chloride dihydrate and 0.2 mg/ml of dopamine hydrochloride) was prepared using a 1.2 mg/ml Tris HCl solution (pH=8.5). DHVs were placed in a clean six-well plate and flattened, with 3 valves in each well, and 4 ml of the mixed solution was added to each well, and reacted in a constant-temperature shaker at 37° C. and 110 rpm for 24 h. The copper chloride-dopamine hydrochloride mixed solution was removed, an obtained reaction product was rinsed with PBS for 24 h, where the PBS was changed once every 6 h, and a resulting rinsed DHV was placed in a sterile PBS solution containing double antibodies at 4° C. for later use (as a Cu group).

S2, preparation of the DHV composite: a 0.5 μg/ml GDF11 solution was prepared with a sterile PBS solution, the copper ion-modified DHV obtained in S1 was placed in a six-well plate and flattened, with 3 valves per well, and each well was added with 4 ml of the GDF11 solution, and reacted for 12 h on a constant-temperature shaker at 37° C. and 110 rpm. The GDF11 solution was removed, an obtained reaction product was rinsed with PBS for 24 h, where the PBS was changed once every 6 h, and a resulting rinsed DHV was placed in a PBS solution containing double antibodies at 4° C. for later use, to obtain the DHV composite (as a GDF11 group).

The DHV was a decellularized porcine aortic valve. A preparation method of the decellularized porcine aortic valve may include: a porcine aortic valve was placed in a six-well plate, with 3 valves per each well, and a Tris-HCl solution (40 mmol/L, pH=7.8) was used to prepare a working solution 1 containing 20 g/L CHAPS and 2 mmol/L TnBP, 4 ml of the working solution 1 was added to each well, and then treated with continuous shaking at 37° C. for 24 h. The Tris-HCl solution (40 mmol/L, pH=7.8) was used to prepare a working solution 2, containing 20 g/L of CHAPS, 2 mmol/L of TnBP, 10 g/L of ASB-14, and 20 g/L of SB 3-10, 4 ml of the working solution 2 was added to each well, the shaking treatment was continued for 24 h, and an obtained product was rinsed 3 times with sterile PBS. The Tris-HCl solution (40 mmol/L, pH=7.8) was used to prepare a working solution 3 containing 1 mmol/L of magnesium chloride and 100 units/ml of totipotent nuclease, 4 ml of the working solution 3 was added to each well, and then treated with continuous shaking for 24 h. An obtained product was rinsed with sterile PBS 3 times for 6 h in each time to obtain a DHV, and the DHV was stored in antibiotic-containing PBS at 4° C. for later use.

As shown in FIG. 1, the DHV composite obtained in S1 of the present disclosure changed from milky white translucent to brownish black. By observation under SEM, it was seen that the wavy fiber structure of the DHV disappeared, and a large number of spherical "nanometer flowers" were formed on the surface. The energy spectrum showed that the surface copper element signal of the DHV composite in the Cu group was significantly enhanced. These results indicated that the copper ion-modified DHV was constructed successfully.

Figure 2A:
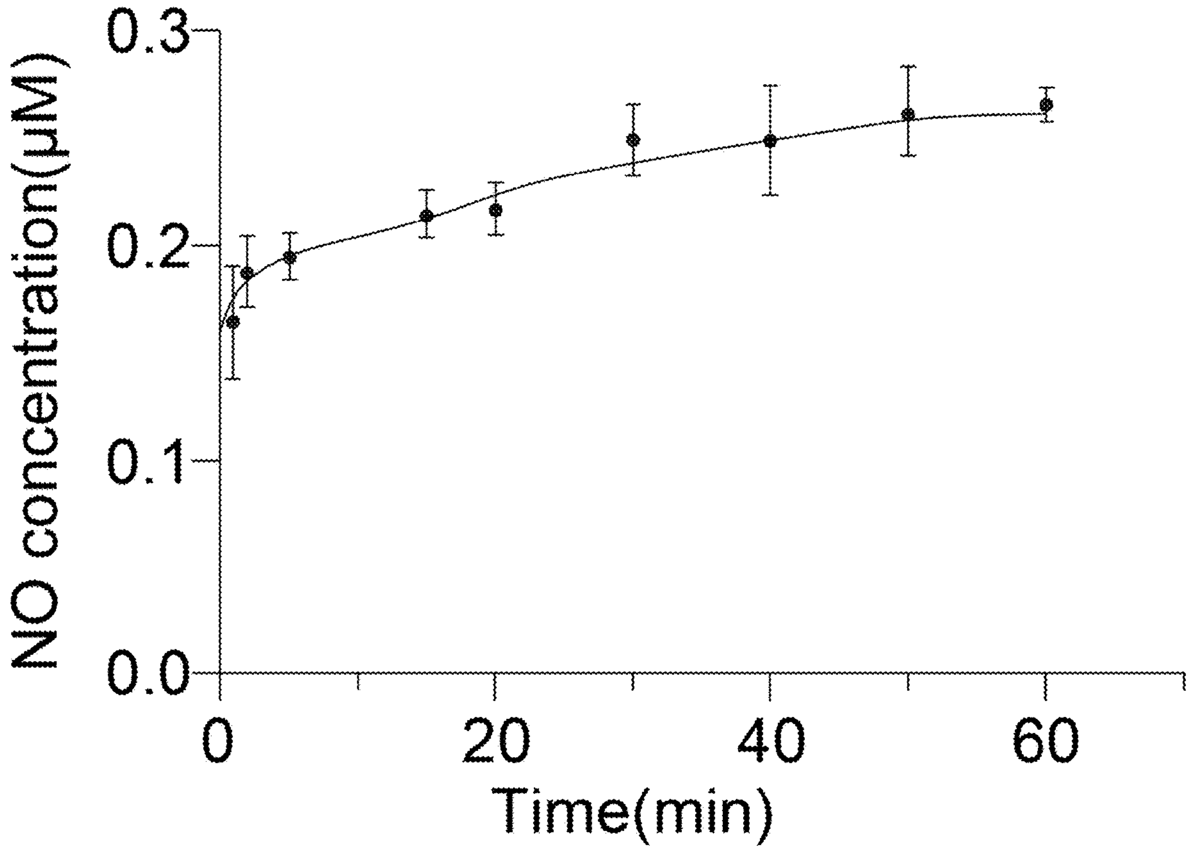
FIG. 2A shows a nitric oxide release after the DHV composite is contacted with a donor according to an embodiment of the disclosure
Figure 2B:
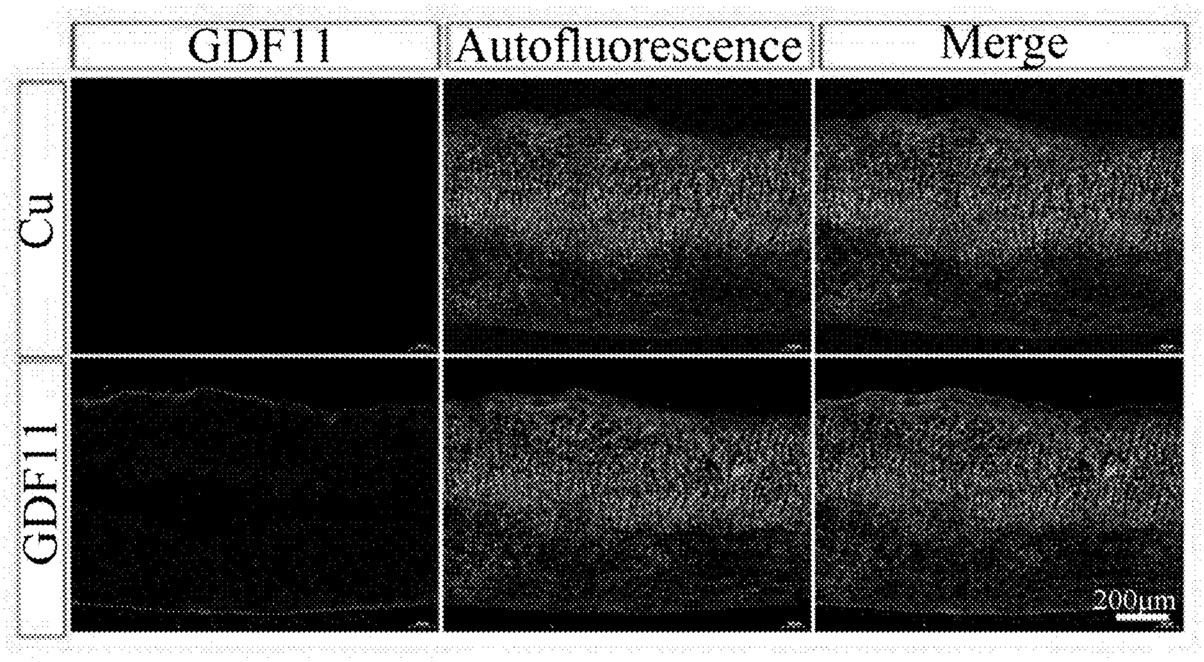
FIG. 2B shows a GDF11 immunofluorescence staining photo of the DHV composite according to an embodiment of the disclosure.
Figure 3A:
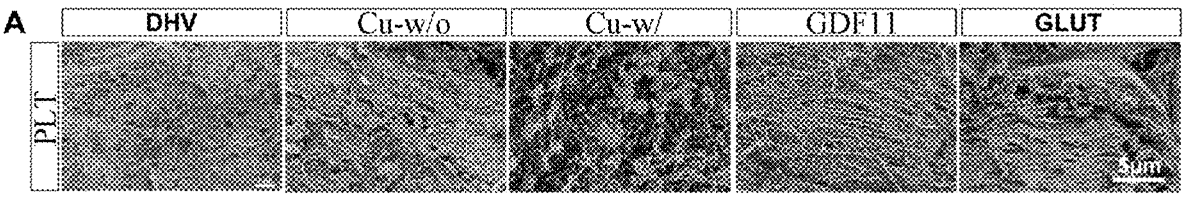
FIG. 3A show an in vitro hemocompatibility experiment of the DHV composite, including an electron micrograph of adherent platelets on a surface of the DHV composite according to an embodiment of the disclosure.
Figure 3B:
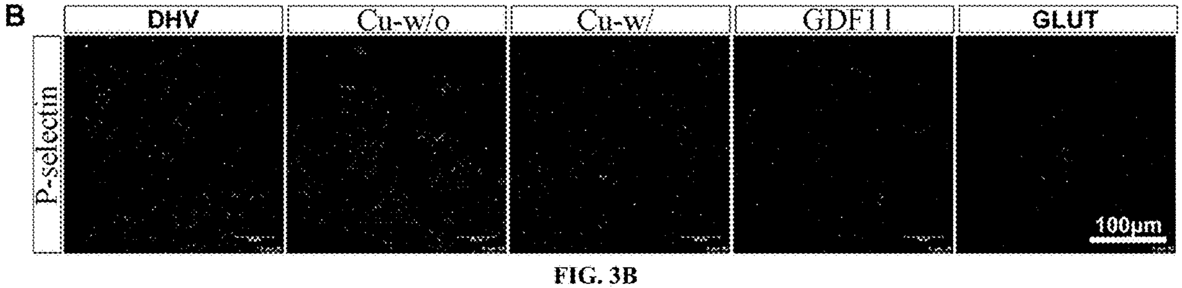
FIG. 3B shows an in vitro hemocompatibility experiment of the DHV composite, including a P-selectin immunofluorescence photo on the surface of the DHV composite according to an embodiment of the disclosure.
Figure 3C:
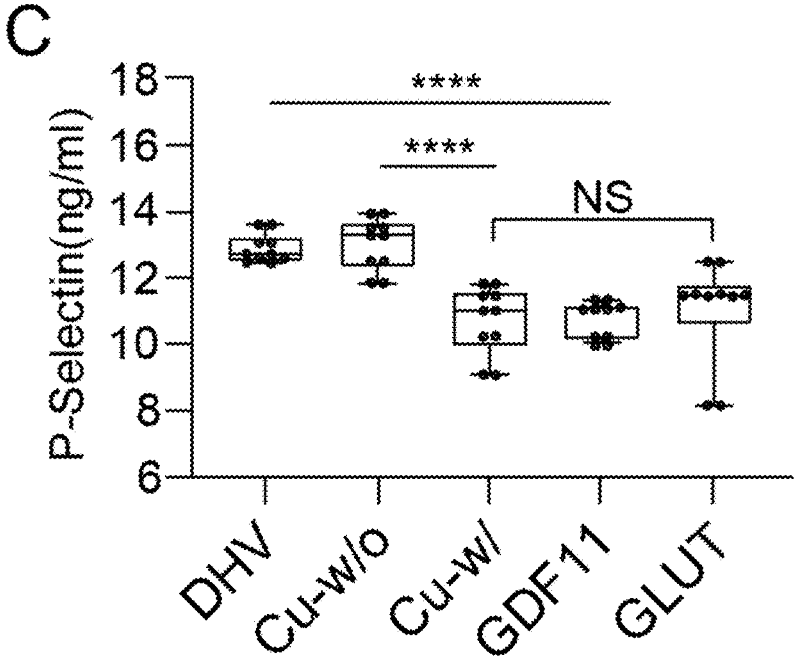
FIG. 3C shows an in vitro hemocompatibility experiment of the DHV composite, including expression levels of P-selectin the DHV composite according to an embodiment of the disclosure.
Figure 3D:
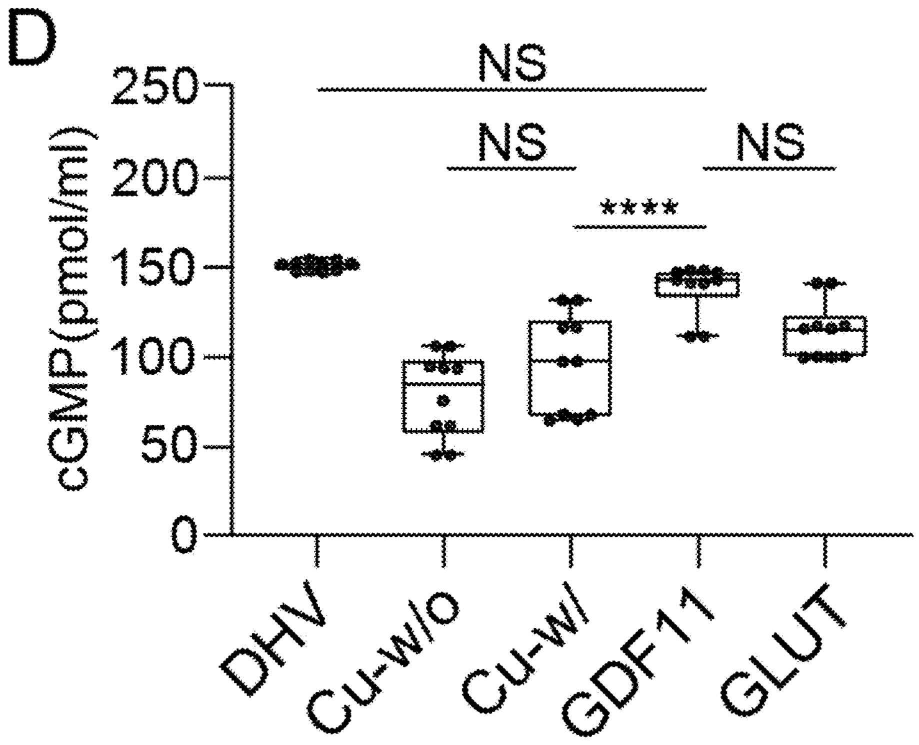
FIG. 3D shows an in vitro hemocompatibility experiment of the DHV composite, including expression levels cGMP of the DHV composite according to an embodiment of the disclosure.
Figure 3E:
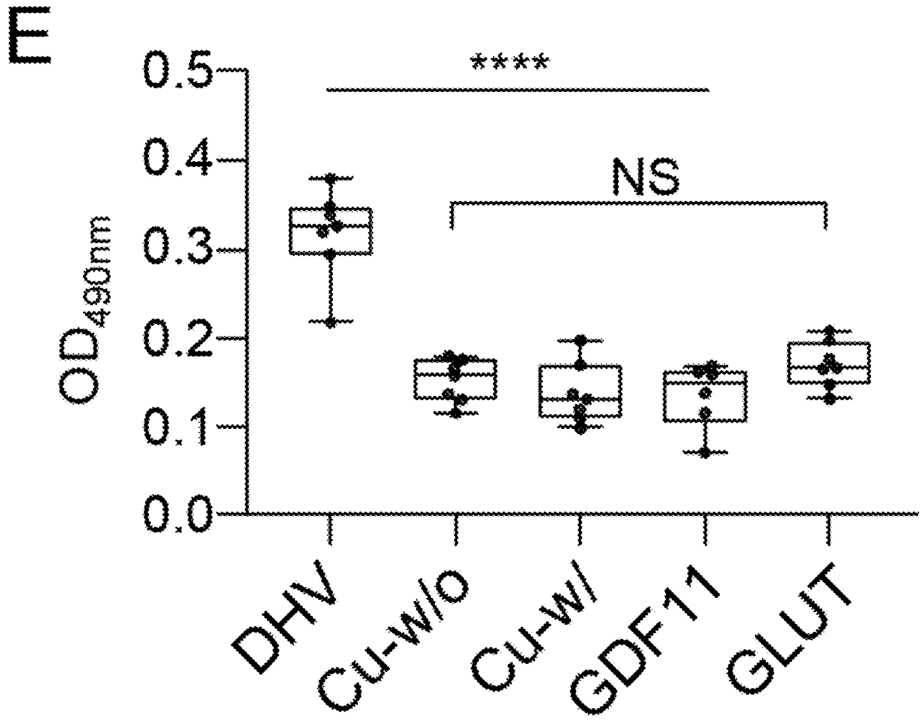
FIG. 3E shows an in vitro hemocompatibility experiment of the DHV composite, including a quantitative statistical graph of adherent platelets of the DHV composite according to an embodiment of the disclosure.
Figure 4A:
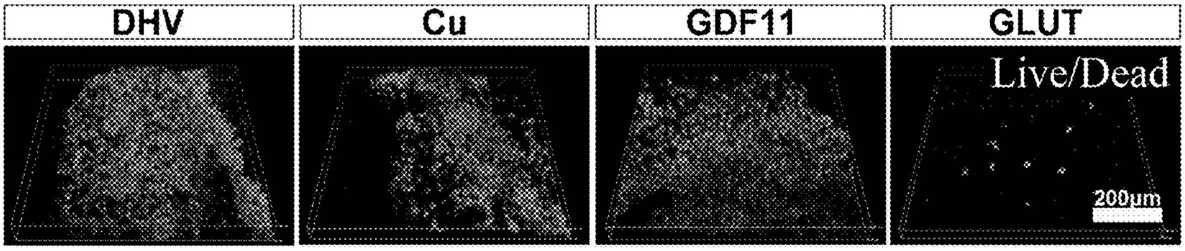
FIG. 4A show an in vitro cytocompatibility experiment of the DHV composite, including a surface HUVECs live/dead cell staining photo of the DHV composite according to an embodiment of the disclosure.
Figure 4B:
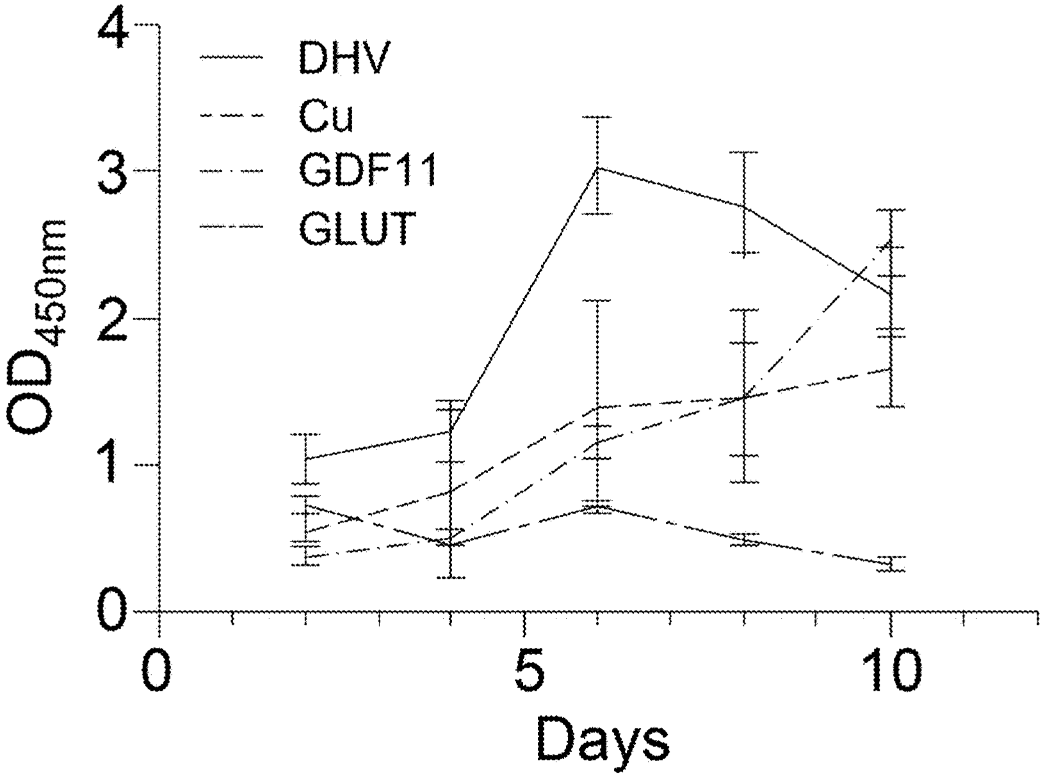
FIG. 4B show an in vitro cytocompatibility experiment of the DHV composite, including a HUVECs growth curve in a fluid environment according to an embodiment of the disclosure.
Figure 4C:
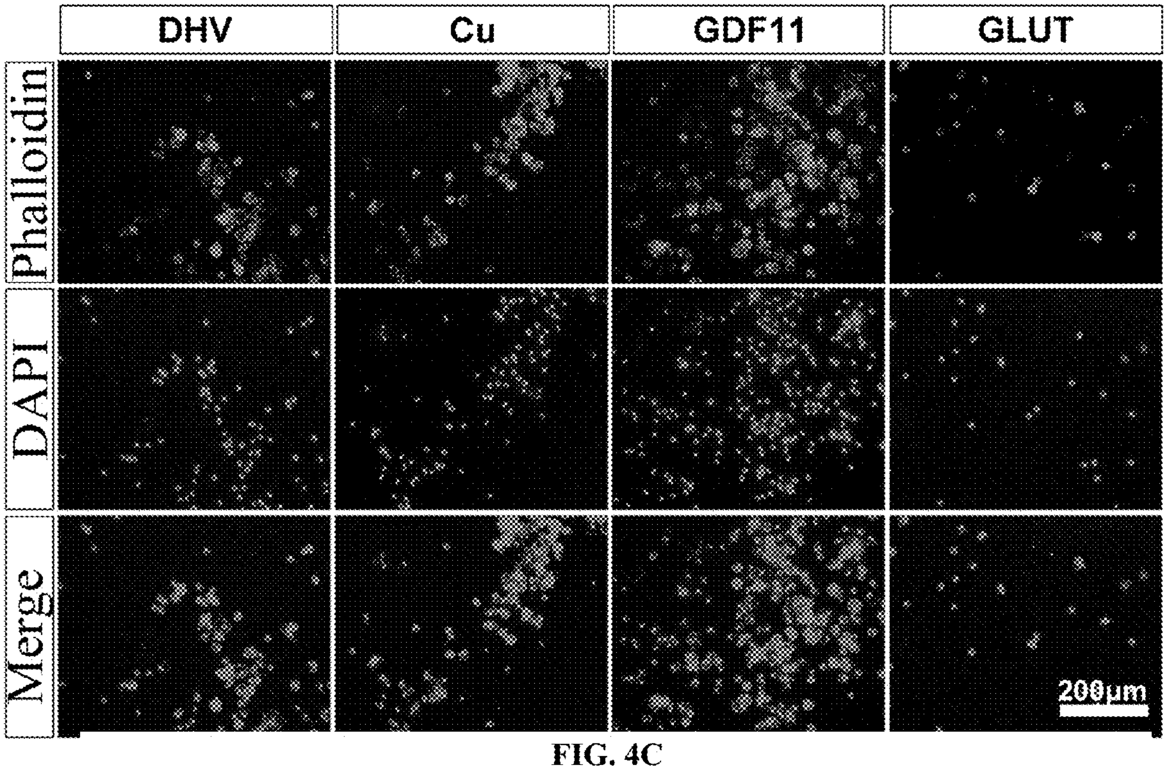
FIG. 4C show an in vitro cytocompatibility experiment of the DHV composite, including a skeleton staining photo according to an embodiment of the disclosure.
Figure 4D:
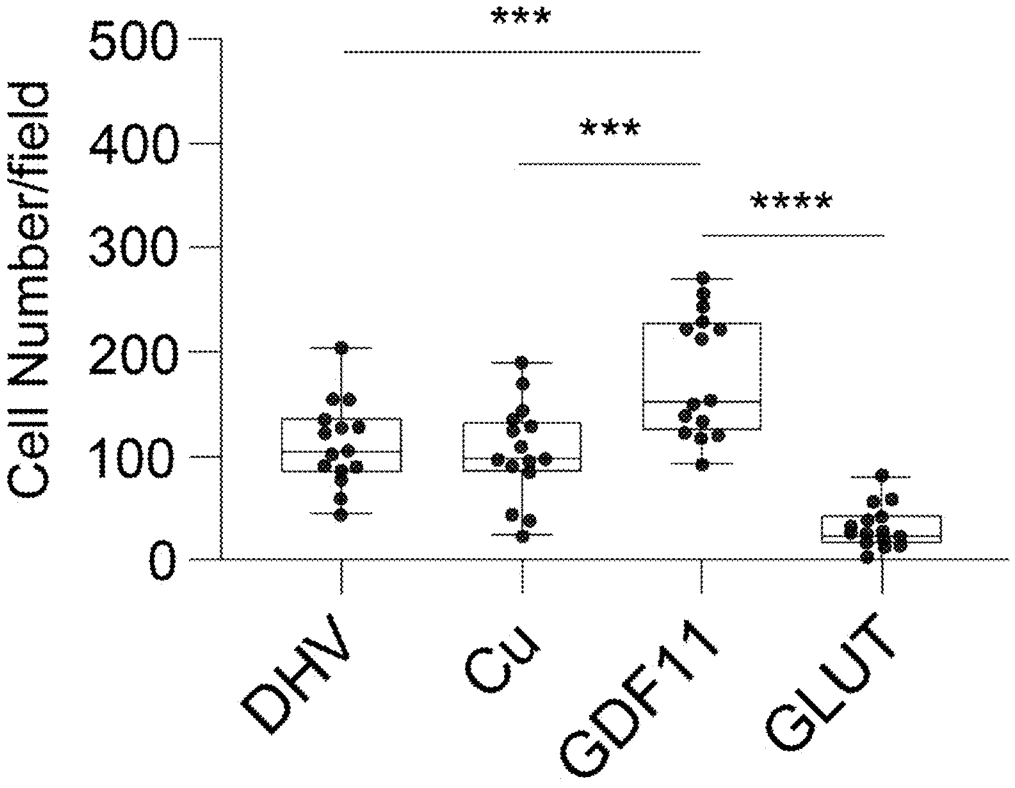
FIG. 4D show an in vitro cytocompatibility experiment of the DHV composite, including a quantitative statistical graph of EPCs cells captured by the DHV composite in a fluid environment according to an embodiment of the disclosure.

As shown in FIGS. 2A-B, the DHV composite catalyzed the generation of nitric oxide immediately after contacting the nitric oxide donor, indicating that the DHV composite could play the function of catalyzing the generation of nitric oxide. Positive fluorescence (red) of GDF11 was seen on the surface of the DHV composite, indicating that the GDF11 had been successfully modified to the DHV composite.

The performance testing was conducted on the DHV composite prepared above:

Item I: Blood Compatibility

Methods: the DHV composite was made into a small disc with a diameter of 7.92 mm, while DHV and glutaraldehyde cross-linked bioprosthesis (GLUT group) were used as controls. According to whether nitric oxide donor was added or not, the copper ion-modified DHV composites were divided into two groups: a group with donor (Cu-w/) and a group without donor (Cu-w/o). Anticoagulant operation was conducted with an ACD anticoagulant, fresh peripheral blood of SD rats was collected, platelet-rich serum was separated, and then incubated with the DHV composite at 37° C. for 1 h. An obtained supernatant was collected, and expression levels of P-selectin and cGMP were detected by an ELISA kit. After incubation, the DHV composite was rinsed 3 times with PBS. One half of the samples were selected for 2.5% glutaraldehyde fixation, ethanol gradient dehydration, tert-butanol replacement, freeze-drying, and gold spraying, and observed under SEM; and the other half of the samples were assayed for the number of adherent platelets by a lactate dehydrogenase kit.

Results: as shown in FIGS. 3A-E, a large number of platelets adhered to the surface of the control group, fused with each other into sheets, and most of which were activated platelets protruding pseudopodia around them. However, there was a highly small number of adherent platelets on the surface of the DHV composite provided by the present disclosure, most of which were in the shape of unactivated discs. Moreover, the DHV composite provided by the present disclosure significantly reduced the expression level of P-selectin and up-regulated the expression level of cGMP after adding the nitric oxide donor. The above results indicated that the DHV composite provided by the present disclosure had the ability of anti-platelet activation and adhesion as well as anti-thrombosis, and showed better blood compatibility.

Item II: Cell Compatibility

Methods: human umbilical vein endothelial cells (HUVECs) were planted on the surface of the DHV composite, stained with a live/dead cell staining kit to distinguish living cells from dead cells, and a cell viability of the HUVECs on the valve surface was detected by a CCK-8 method. Bone marrow endothelial progenitor cells (EPCs) were extracted from SD rat tibia. The ibidi bioreactor was used to construct a fluid environment, and an obtained system was filled with a suspension of the EPCs for dynamic culture. The cytoskeleton of EPCs captured on the surface of the DHV composite was labeled with phalloidin, and the nuclei were stained with DAPI and counted.

Results: as shown in FIGS. 4A-D, there was a highly small number of living cells (green) in the GLUT of the control group, indicating high cytotoxicity. However, the living cells on the surface of the DHV composite in the present disclosure had formed a relatively complete endothelial cell layer, and no obvious dead cells (red) were seen, indicating desirable cytocompatibility. Compared with the control group, the number of EPCs captured on the surface of the DHV composite was significantly increased, indicating that the DHV composite could capture EPCs cells in the fluid under a dynamic environment, to promote the endothelialization of the DHV composite.

Item III: Mechanical Properties

Methods: the DHV composite was cut into strip samples with a length of about 20 mm and a width of about 3 mm along the circumference, and the width and thickness were measured and recorded with a vernier caliper. The samples were fixed on a sample holder of a mechanical tester, an initial gauge length was measured with the vernier caliper, and the samples were stretched to both ends at a uniform speed (100 N, 5 mm/min) at room temperature until the samples were broken. A stress-strain curve was recorded at this time, and the Young's modulus and ultimate tensile strength were calculated.

Figure 5A:
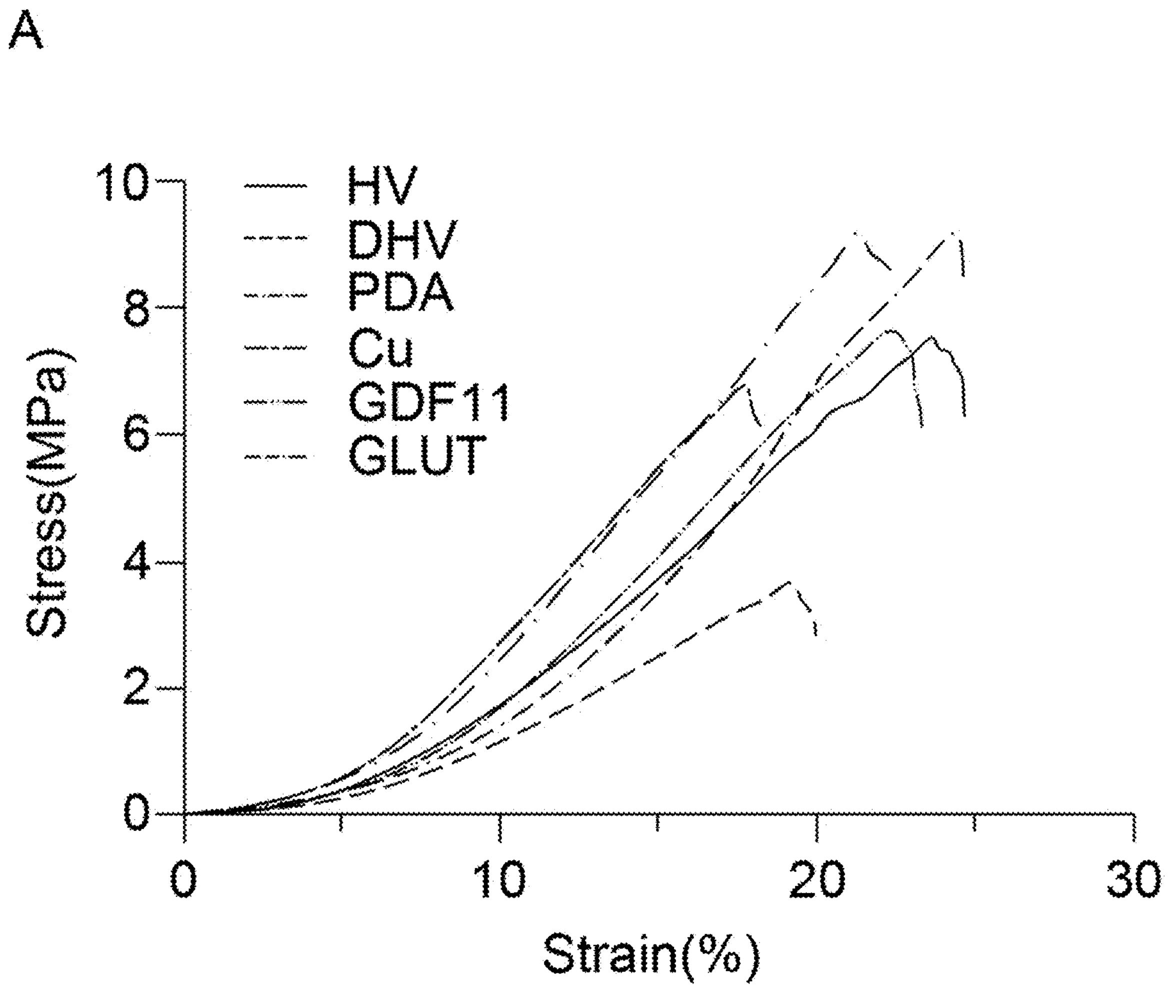
FIG. 5A shows a mechanical property testing result of the DHV composite showing a stress-strain graph according to an embodiment of the disclosure.
Figure 5B:
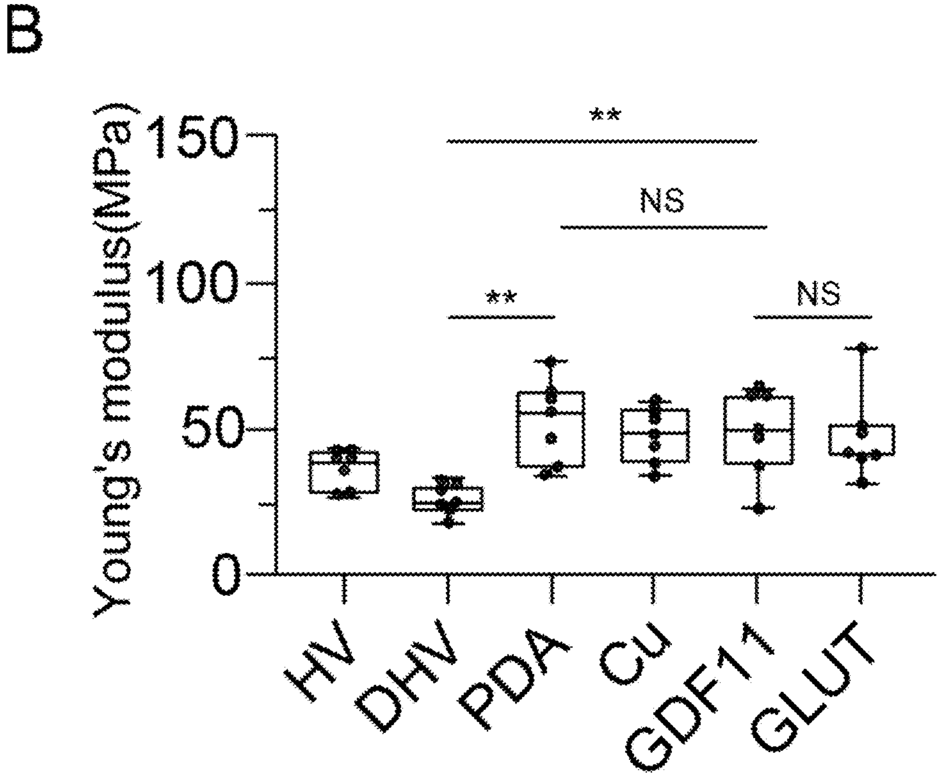
FIG. 5B shows a mechanical property testing result of the DHV composite showing a Young's modulus graph according to an embodiment of the disclosure.
Figure 5C:
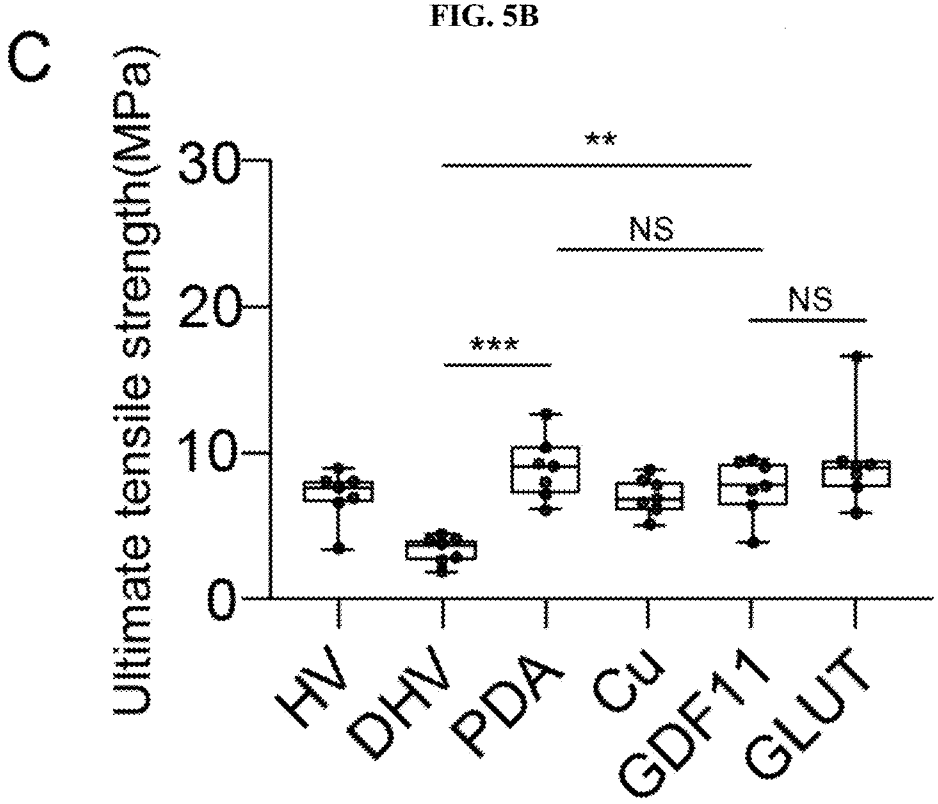
FIG. 5C shows a mechanical property testing result of the DHV composite showing an ultimate tensile strength graph according to an embodiment of the disclosure.

Result: as shown in FIGS. 5A-5C, the Young's modulus and ultimate tensile strength of the DHV composite in the present disclosure were significantly enhanced compared with those of the DHV group, reaching a level comparable to those of the valve composite of the GLUT group, indicating excellent mechanical properties of the DHV composite.

Item IV: In Vivo Remodeling and Regeneration

Methods: the DHV composite was cut into pieces of 5 mm×4 mm, sewn into a tube under a microscope, and anastomosed to the abdominal aorta of SD rats. After 2 weeks and 4 weeks, the patency was detected by ultrasound, and the specimens were taken out for Masson staining, von Kossa staining, CD31 staining, vWF staining, α-SMA staining, and collagen immunofluorescence staining.

Figure 6:
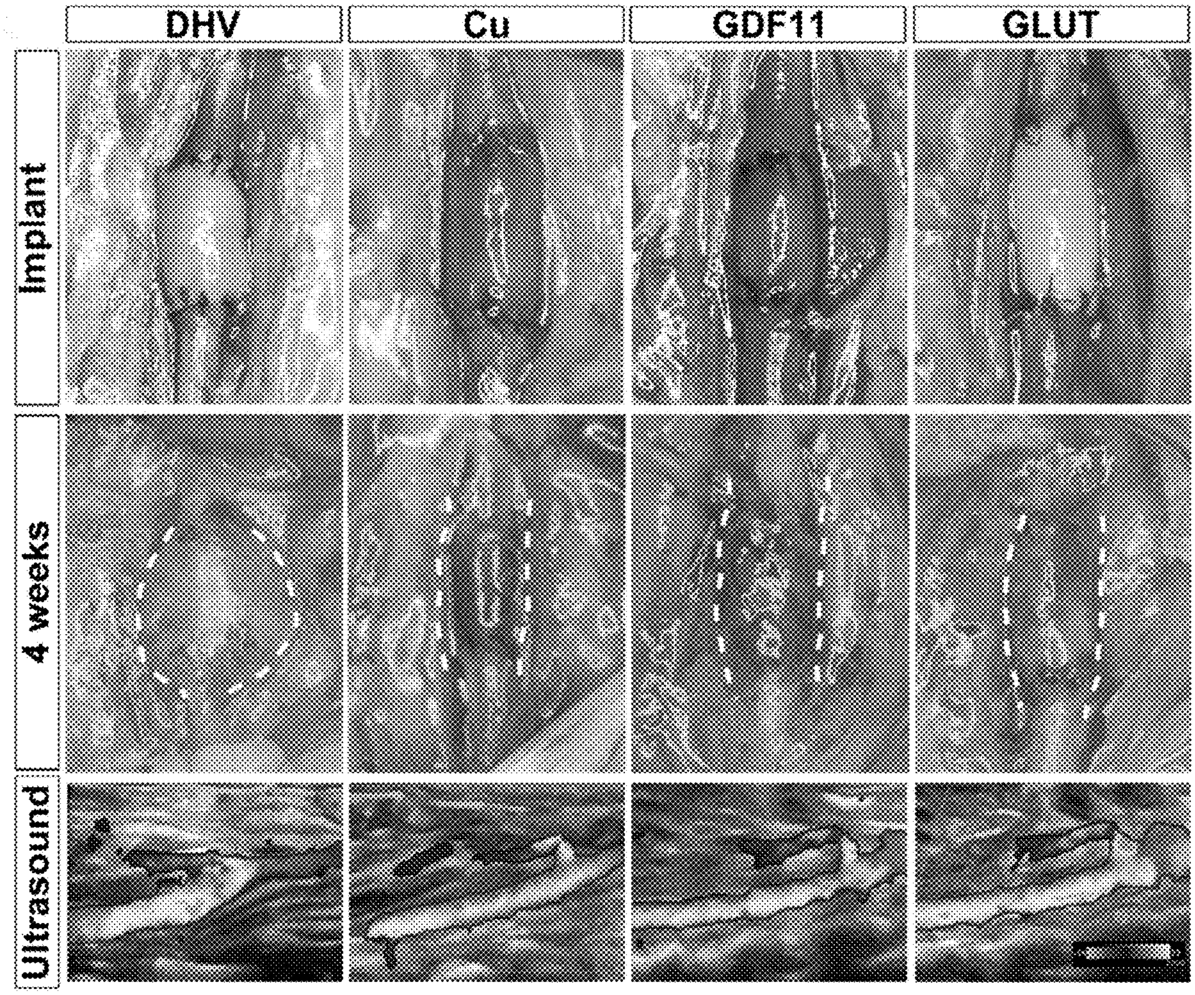
FIG. 6 shows a general photo and an ultrasonic photo after the DHV composite is anastomosed to abdominal aorta of rats according to an embodiment of the disclosure.
Figure 7:
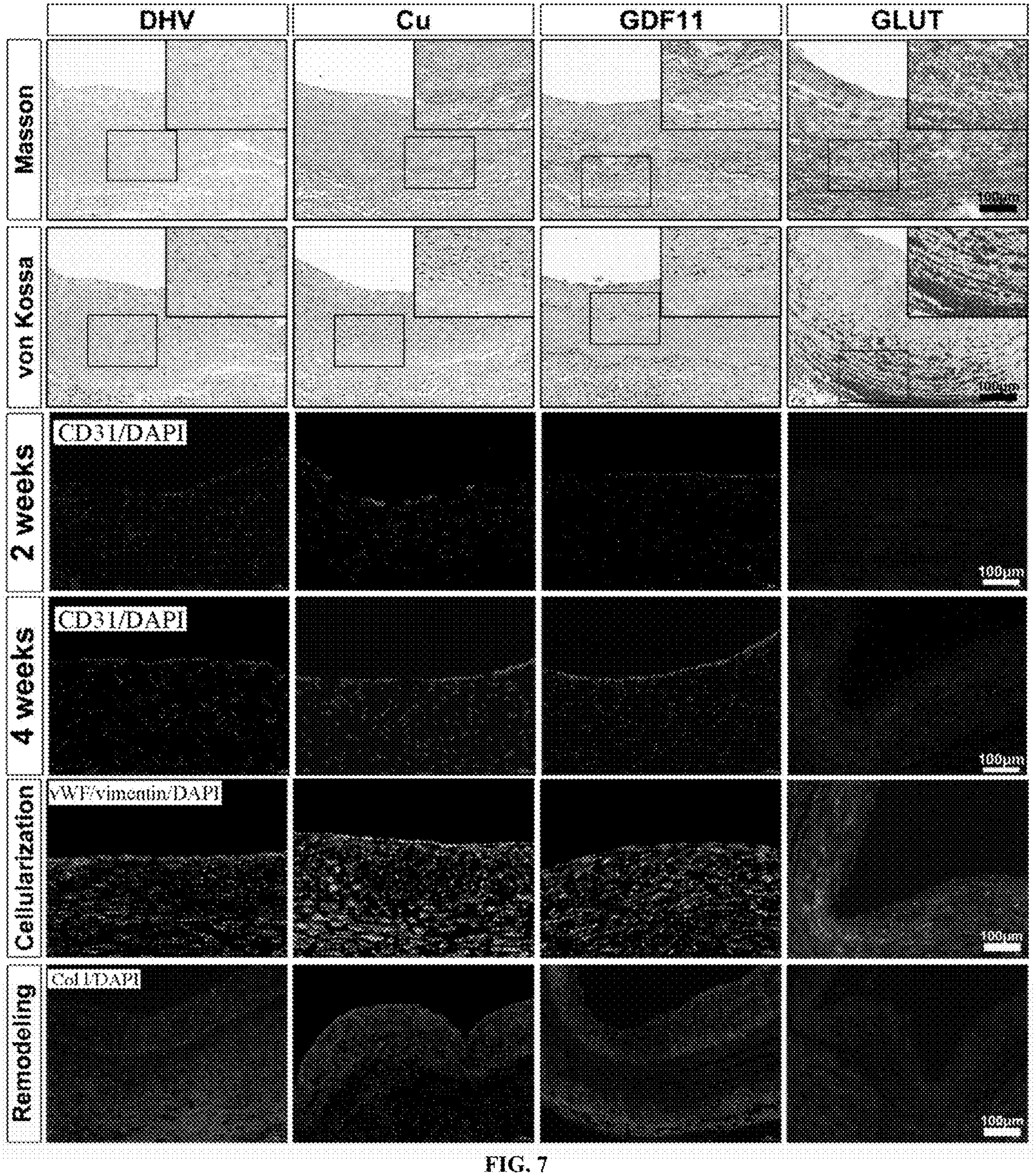
FIG. 7 shows histological staining photos after the DHV composite is anastomosed to abdominal aorta of rats, including a Masson staining photo, a vonKossa staining photo, an endothelial cell immunofluorescence staining photo, an interstitial cell immunofluorescence staining photo, and a new collagen staining photo according to an embodiment of the disclosure.
Figure 8:
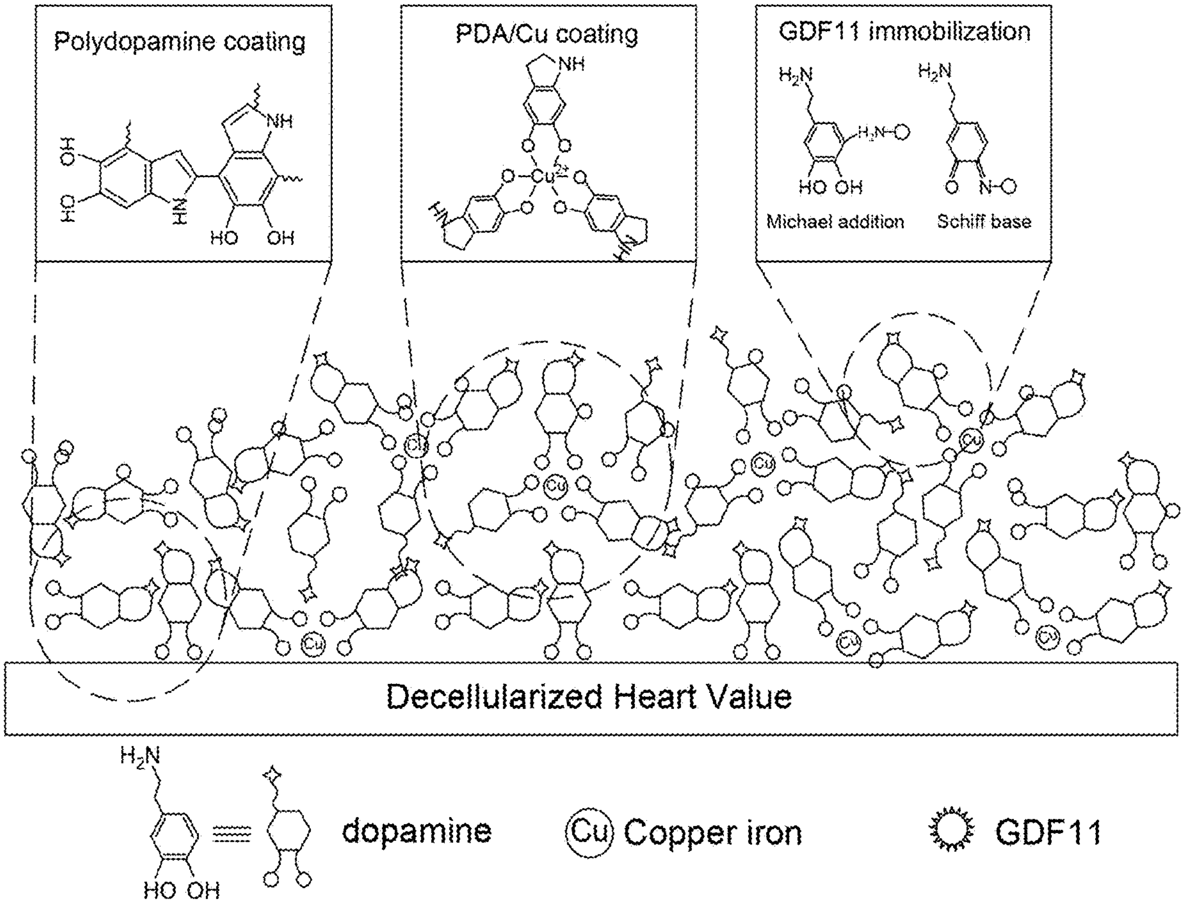
FIG. 8 shows a chemical reaction principle of the DHV composite according to an embodiment of the disclosure.

Results: as shown in FIG. 6, 4 weeks after the DHV composite was implanted into the abdominal aorta of rats, the lumen of the DHV group was significantly expanded, indicating that the material in the DHV group had insufficient mechanical properties and an excessively high degradation rate. However, the DHV composite in the present disclosure remained unobstructed and did not expand, indicating that the DHV composite showed better mechanical properties and blood compatibility. The DHV composite was taken out for staining, as shown in FIG. 7. The results of Masson staining showed that the valve composite in the DHV group had obvious cell (red) infiltration, and the collagen fibers (blue) were basically completely degraded; the valve composite in the GLUT group hardly degraded, no obvious cell infiltration occurred, and the collagen fibers were still highly dense. However, the DHV composite in the present disclosure was moderately degraded, and cell infiltration and partial collagen fiber degradation were seen, with a speed significantly slower than that of the DHV group. The von Kossa staining showed that the material in the GLUT group had large calcification nodules, while the DHV composite in the present disclosure did not have obvious calcification. After CD31 staining of endothelial cells, the DHV composite in the present disclosure had obvious CD31-positive endothelial layer formation at 2 weeks, while no obvious endothelialization was seen in the control group at this time. Moreover, the DHV composite in the present disclosure showed a higher degree of endothelialization than that in the control group at 4 weeks, indicating that the DHV composite in the present disclosure may effectively accelerate the endothelialization. The vWF and α-SMA staining also showed that the DHV composite in the present disclosure had experienced host cell infiltration, and its cell type and distribution were similar to those of natural valves; while collagen staining showed that the DHV composite in the present disclosure showed visible new collagen production. This indicated that the DHV composite in the present disclosure underwent a certain degree of degradation and remodeling after being implanted in the body, and had an ability to regenerate in vivo; while the material in the GLUT group did not have this process, and did not show the ability to regenerate.

It will be clear to those skilled in the art that various modifications to the above examples may be made without departing from the general spirit and concept of the present disclosure. These modifications shall all fall within the protection scope of the present disclosure. The claimed protection schemes of the present disclosure shall be determined by the claims.

Various embodiments of the disclosure may have one or more of the following effects. In some embodiments, the DHV composite according to the present disclosure may generate endogenous nitric oxide by contacting with a nitric oxide donor in the blood, may have an excellent anti-platelet performance, and may inhibit thrombus formation in vivo. In other embodiments, the DHV composite according to the present disclosure may show an ability to capture endothelial progenitor cells in the blood and may play a relatively strong role in promoting the endothelialization of a valve composite. In further embodiments, the present disclosure may provide a DHV composite, a preparation method, and a use thereof. A main purpose in these embodiments of the discourse may be to provide a valve composite with desirable blood compatibility and in vivo remodeling and regeneration capabilities to avoid the poor compatibility and inability to grow in vivo for the existing valve substitutes.

In some embodiments, the present disclosure may provide a DHV composite which has a nitric oxide catalytic activity and which may produce endogenous nitric oxide after contacting with a nitric oxide donor in the blood. The experimental results show that the DHV composite may show strong anti-platelet properties and may inhibit thrombus formation in vivo.

In other embodiments, the present disclosure may provide a DHV composite which has the ability to capture endothelial progenitor cells in blood. The results of cell experiments show that the DHV composite has a stronger ability to recruit and capture endothelial progenitor cells in a fluid environment. In vivo experiments show that the DHV composite has a strong promoting effect on the formation of endothelialization after DHV implantation.

In further embodiments, the present disclosure may provide a DHV composite which shows desirable biocompatibility. Moreover, compared with the existing biological valves, the DHV composite may have accelerated cellularization, moderate degradation and remodeling, and no calcification during in vivo experiments. The DHV composite may have the ability to remodel and regenerate, may grow with the human body after implantation, and may have application prospects especially in children patients.

In some embodiments, the present disclosure may be different from the existing 3D-printed TEHV scaffolds. In the present disclosure, HVs with the ability to remodel and regenerate may be prepared directly from natural DHVs. The natural DHV may be derived from other organisms, thus solving the problem of biocompatibility. Moreover, the natural DHV has a more complex and fine three-dimensional structure, which may better guide the growth of cells and the remodeling and regeneration of tissues.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A preparation method of a decellularized heart valve (DHV) composite, comprising the following steps:

S1, conducting a reaction I on a DHV with a copper chloride-dopamine hydrochloride mixed solution to obtain a copper ion-modified DHV; and S2, conducting a reaction II on the copper ion-modified DHV with a growth differentiation factor 11 (GDF11) solution to obtain the DHV composite.

2. The preparation method of a DHV composite according to claim 1, wherein step S1 specifically comprises the following steps:

S11, mixing the DHV with the copper chloride-dopamine hydrochloride mixed solution, and conducting the reaction I;

S12, removing the copper chloride-dopamine hydrochloride mixed solution, and rinsing an obtained reacted DHV with a rinsing solution; and S13, obtaining the copper ion-modified DHV.

3. The preparation method of a DHV composite according to claim 2, wherein the copper chloride-dopamine hydrochloride mixed solution has a pH value of 8 to 9, preferably 8.5; and the copper chloride-dopamine hydrochloride mixed solution has 0.005 mg/ml to 0.2 mg/ml, preferably 0.1 mg/ml of $CuCl_2 \cdot 2H_2O$ and 0.1 mg/ml to 5 mg/ml, preferably 0.2 mg/ml of dopamine hydrochloride.

4. The preparation method of a DHV composite according to claim 2, wherein after the DHV is mixed with the copper chloride-dopamine hydrochloride mixed solution, a resulting mixture I is subjected to the reaction I in an environment of 25° C. to 40° C.; preferably, after the DHV is mixed with the copper chloride-dopamine hydrochloride mixed solution, the mixture I is subjected to the reaction I in any constant temperature of 36° C. to 37.5° C., preferably 37° C.

5. The preparation method of a DHV composite according to claim 2, wherein step S2 specifically comprises the following steps:

S21, mixing the copper ion-modified DHV obtained in step S1 with the GDF11 solution prepared by a PBS solution, and conducting the reaction II;

S22, removing the GDF11 solution, and rinsing an obtained reacted copper ion-modified DHV with a rinsing solution; and S23, obtaining the DHV composite.

6. The preparation method of a DHV composite according to claim 5, wherein in step S21, the GDF11 solution has a concentration of 0.5 ug/ml; and in step S21, after the copper ion-modified DHV is mixed with the GDF11 solution prepared by the PBS solution, a resulting mixture II is subjected to the reaction II in any constant temperature of 36° C. to 37.5° C., preferably 37° C.

7. The preparation method of a DHV composite according to claim 6, wherein in steps S12 and S22, the rinsing solution is a PBS solution, and the rinsing is performed by a process comprising: placing the reacted DHV or the reacted copper ion-modified DHV in a constant-temperature shaker, washing with a sterile PBS solution for 24 h, and changing the sterile PBS solution once every 6 h; in steps S11, S12, S21, and S22, the constant-temperature shaker has an oscillation frequency of 110 rpm; and in step S1, the DHV is a natural DHV.

* * * * *